United States Patent [19]

Law et al.

[11] 4,278,440
[45] Jul. 14, 1981

[54] REAGENT AND METHOD FOR DIRECT DETERMINATION OF CHLORIDE IN SERUM

[75] Inventors: Wai-Tak Law, Rye, N.Y.; Gerhard Ertingshausen, Greenwich, Conn.

[73] Assignee: Union Carbide Corporation, New York, N.Y.

[21] Appl. No.: 118,215

[22] Filed: Feb. 4, 1980

[51] Int. Cl.³ ............................................ G01N 33/52
[52] U.S. Cl. .................................... 23/230 B; 252/408
[58] Field of Search ..................... 23/230 B, 230 R; 252/408

[56] References Cited

U.S. PATENT DOCUMENTS 3,185,549  5/1965  Hamilton .................... 252/408 X

OTHER PUBLICATIONS

West et al., *Anal. Chem.*, 28 (1956) pp. 1834–1838.
Fingerhut, *Clin. Chem. Acta.*, 41, 247 (1972).

*Primary Examiner*—Arnold Turk
*Attorney, Agent, or Firm*—J. Hart Evans

[57] ABSTRACT

A direct, quantitative method is provided for the determination of chloride in blood serum which is based on the reaction between the chloride and ferric ions. A novel reagent is employed in the method which contains no mercury but does contain a surfactant which prevents protein precipitation.

8 Claims, 1 Drawing Figure

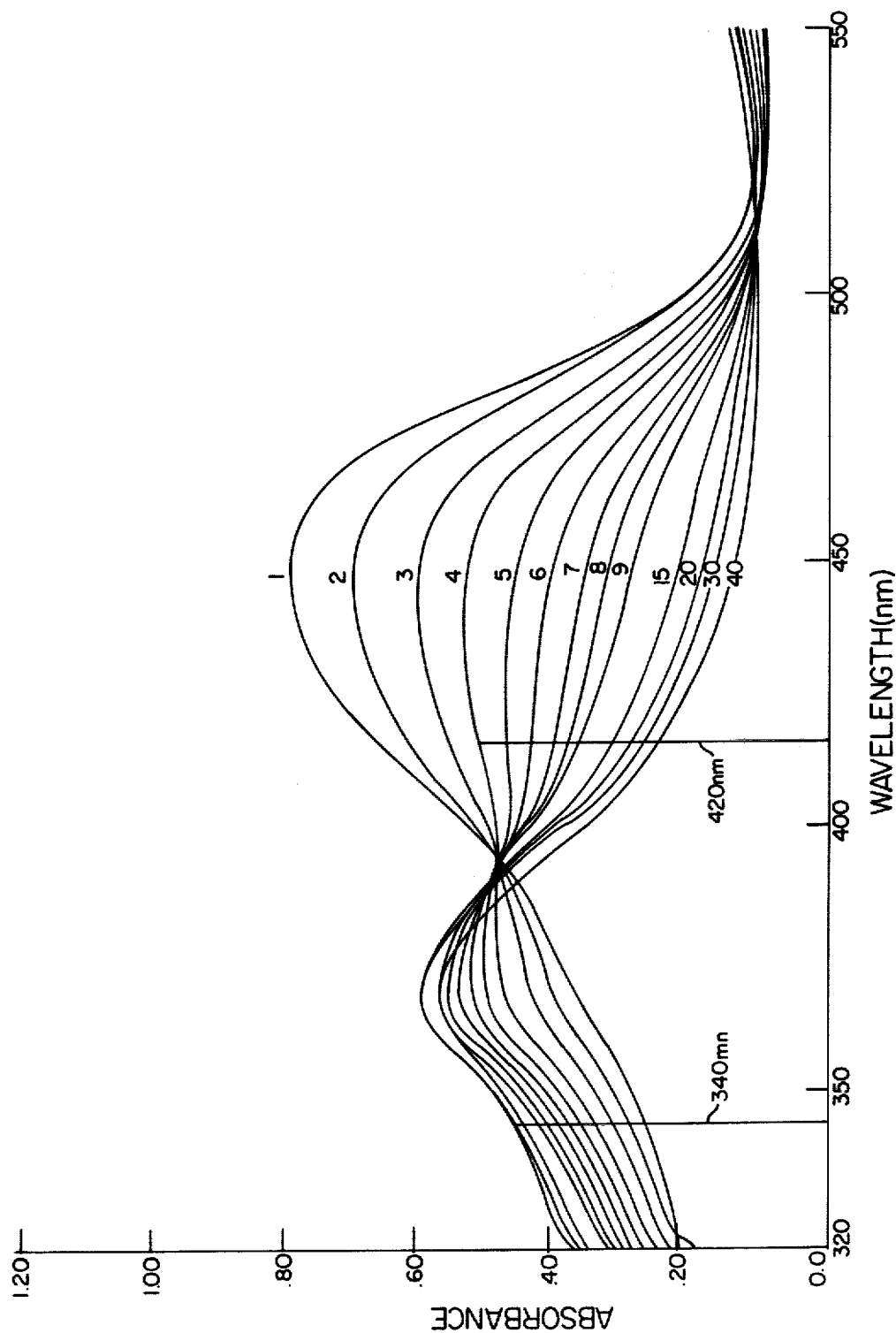

REAGENT AND METHOD FOR DIRECT DETERMINATION OF CHLORIDE IN SERUM

FIELD OF THE INVENTION

This invention relates to a reagent and method for the direct quantitative determination of chloride in blood serum.

DESCRIPTION OF THE PRIOR ART

It has long been known in the biological sciences that chloride is the major extracellular anion in biological fluids. Movement of the chloride into and out of the red cell is essential for transport of bicarbonate ions in response to changing amounts of carbon dioxide. Elevated chloride values in serum usually indicate dehydration, hyperventillation, congestive heart failure, prostatic or other types of urinary obstruction. Low serum chloride values are found with extensive burns, excessive vomiting, metabolic acidosis, nephritis, intestinal obstruction, Addisonian crisis and diarrhea.

The earliest practical technique for chloride analysis was reported by T. Volhard in 1974 (J. Prakt. Chem., 9 217 (1974)). Since that time, dozens of direct and indirect methods of analysis have been reported in the literature. The most popular methods are the coulometric titration, the specific-ion electrode technique and the colorimetric mercuric thiocyanate method.

P. W. West and H. Coll reported in Anal. Chem., 28 (1956) a direct spectrophotometric method for chloride in the 0.02–0.2 meq/L range. B. Fingerhut later adopted this non-mercurimetric method for serum chloride analysis as reported in Clin. Chem. Acta., 41, 247 (1972). Since the reagent is in a strong perchloric acid medium, dialysis was employed to prevent problems due to protein precipitation. The method did not gain wide acceptance in the clinical laboratory, yet the direct colorimetric method contains no mercury that causes undesirable disposal problems as in other colorimetric methods. It should also be noted that in the original West and Coll article, no observable absorbance change was reported below an acid concentration of 2.0 N.

It has now been found that by utilizing a mercury-free reagent which contains ferric perchlorate and perchloric acid in dilute quantities and preferably, in the presence of a non-ionic surfactant, reliable results can be achieved in the direct, quantitative determination of chloride.

Accordingly, one or more of the following objects can be achieved by the practice of this invention. It is an object of this invention to provide a novel reagent and method for the direct, quantitative determination of chloride in serum. Another object is to provide a reagent for chloride determination which utilizes the reaction between the chloride and ferric ions. A still further object of this invention is to provide a reagent which does not contain mercury. Another object is to provide a method which employs a reagent containing perchloric acid at concentrations lower than those heretofore used. A still further object of this invention is to provide a method for the determination of chloride which has a high linearity range for chloride ion determination. Another object of this invention is to provide a method for the determination of chloride ion which circumvents interference by components present in blood serum. A further object of this invention is to provide a bichromatic method which facilitates chloride determination on a centrifugal spectrophotometric analyzer.

These and other objects will readily become apparent to those skilled in the art in the light of the teachings herein set forth.

SUMMARY OF THE INVENTION

In its broad aspect this invention is directed to a reagent and method for the direct, quantitative determination of chloride in serum. The method, employing the reagent, is comprised of the steps of:

(a) contacting a sample of serum with the reagent to form a solution wherein the reagent contains:
  (i) from about 0.01 N to about 2.0 N perchloric acid in deionized water,
  (ii) from about 0.01 N to about 1.0 N ferric perchlorate in deionized water, and
  (iii) from about 0.1 to about 20 percent by weight of a non-ionic surfactant capable of minimizing protein precipitation while not interfering with absorbance of the solution.
(b) measuring the absorbance of the solution after an incubation period,
(c) comparing the absorbance of the solution with that obtained from solutions containing known amounts of chloride, and
(d) determining the amount of chloride in the serum.

DESCRIPTION OF THE DRAWING

The single drawing depicts a series of spectral scans taken every second on a scanning analytical spectrophotometer after mixing of sample and reagent. As is evident from the scan the absorption caused by bilirubin has a maximum of 450 nm which shifts with time to 370 nm. The absorbance reading taken in 4 seconds at 420 nm equals the final absorbance reading measured at 340 nm.

DESCRIPTION OF THE PREFERRED EMBODIMENT

It has been found that chloride can be determined quantitatively in blood serum by a novel method which utilizes the reaction between chloride and ferric ions in the presence of a non-ionic surfactant. As hereinbefore indicated, the prior art disclosed the use of ferric perchlorate and a 2 N–8.5 N perchlorate acid in the determination of small amounts of chloride in aqueous samples. The yellow chloro complexes of iron (III) exhibit an intense absorption band in the vicinity of 340 nm, while the reagent containing Fe(III) perchlorate in acidic medium absorbs little light in this range, thus lending itself to quantitative measurement.

Perchloric acid is well known to be a good serum protein precipitant. However, in order to determine the chloride concentration in serum, a separation process for serum proteins such as the dialysis method reported by Fingerhut must be employed before the method can be adapted to an automated procedure. Urea has been used to prevent protein precipitation in the perchloric acid medium of a different color reaction, but it was observed that urea formed a color product with the Fe(III) ions near 340 nm and was therefore unsuitable for a direct reaction.

However, in contrast to the prior art methods, it has been found that the ferric perchlorate and perchloric acid can be employed in very dilute concentrations and the use of a surfactant eliminates a separate protein separation step. Hence, through a systematic study of pH dependance of the Fe(III)-chloride complexes, it was discovered that ferric chloride species formed under well defined conditions of low acidity. For example, it was observed that the species absorbs linearly at 340 nm throughout and beyond the physiological range of chloride in serum, the standard curve obeying Beer's Law. The process also gives sensitivity that is comparable to the reagent that contains concentrated perchloric acid. Moreover, it has been observed that in the process of this invention, the chloride complex forms rapidly in less than 1 minute.

As previously indicated the perchloric acid and ferric perchlorate are employed as dilute solutions. The procedure for preparation of the reagent is set forth in Example 1. However, in practice it has been found that the composition of the reagent can be varied to obtain good results with different sensitivity. Therefore, the reagent of this invention can vary in composition as follows:

1. Perchloric Acid ($HClO_4$)—About 0.01 N to about 2.0 N.
2. Ferric Perchlorate, non-yellow $[Fe(ClO_4)]_3$—About 0.01 N to about 1.0 N.
3. Polyoxyethylene Lauryl Ether (or similar nonionic surfactants)—About 0.1% to about 20% by weight.

In actual practice using the particular analyzer hereinafter indicated, the reconstituted reagent contained 0.0378 N $Fe(ClO_4)_3$, 9.65 percent of polyoxyethylene lauryl ether, and 0.246 N $HClO_4$.

As indicated, the process and reagent of this invention utilizes a non-ionic surfactant to surpress and/or eliminate blood protein precipitation. In contrast to the use of urea, the non-ionic surfactant does not form a color product with the Fe(III) ions near 340 nm and hence, is ideally suited for this use.

In practice, the only requirements of the surfactant are that it be non-ionic, that it surpresses or eliminates blood protein precipitation, and, of course, in contrast to urea, that it does not interfere with the absorbance measurement. Preferred surfactants are the family of polyoxyethylene ethers having from 2 to 40 ethylene oxide units and derived from primary and secondary alcohols having from 8 to 18 carbon atoms. A particularly preferred non-ionic surfactant which is well suited for use in this invention is polyoxyethylene lauryl ether sold by Atlas Chemical Industries under the trademark Brij 35. Other non-ionic surfactants can be used as long as they possess the above properties.

Since the reagent employed in this invention is an oxidizing agent which oxidizes bilirubin, it creates a dynamic interference problem for serum samples. From a study of the interference, it was found that the general strategy of serum blanking, chemical modification, as well as separation by extraction were either too complicated or too lengthly. An important feature of the bichromatic procedure of this invention was the use of a 420 nm filter to perform the dynamic blanking procedure. Hence, this invention covers the use of filters from 380–450 nm range for bichromatic blanking purposes. The 420 nm filter is preferred because of its ability to eliminate bilirubin and hemoglobin interferences simultaneously. The serum blank changes with time because the bilirubin absorption peak slowly shifts from 450 nm to 370 nm. A blank absorbance that matches the one measured at 340 nm both for the static hemolysis and the dynamic bilirubin interferences can be obtained at 420 nm with proper timing as determined experimentally and as depicted in the drawing. This serum blank is then stored and subtracted from the final reading taken at 340 nm. This procedure is simple, it circumvents the storing of a serum blank and it eliminates the bilirubin interference problem.

While the method of this invention can be employed with any instrument that has bichromatic measurement capability, it is particularly useful with the CentrifiChem ® analyzer which is marketed by Union Carbide Corporation and utilizes a centrifugal field for the mixing and transfer of reagents. If an analysis is performed manually with a spectrophotometer thermostated at 30° C., a flow-through cell attachment is preferred. With the CentrifiChem analyzer, samples and reagents are pipetted into the transfer disc with a sample dilution factor of 1:40. The analyzer parameters can be dialed in manually or the computer can be programmed to do the automated experimental steps. The disc is placed inside the analyzer, parameters are loaded and spinning started. After the printout, the analyzer is then reset with wavelength changed to produce the final results.

The following examples illustrate the best mode presently contemplated for the practice of this invention:

EXAMPLE 1

Reagent Preparation

A stock solution of ferric perchlorate (0.7 N) was prepared by dissolving 360 grams of ferric perchlorate, non-yellow crystals into 1 liter with deionized water. This solution was then filtered and standardized with potassium dichromate. A 5 N stock solution of perchloric acid was prepared by diluting 450 milliliters of 70 percent perchloric acid with 1 liter of deionized water and standardizing the solution with sodium hydroxide.

The working solutions were prepared as follows: Solution A was prepared from the stock solutions and contained 0.0756 N ferric perchlorate and 0.492 N perchloric acid. Solution B was prepared as an aqueous solution containing 19.3 percent by volume of polyoxyethylene lauryl ether which is marketed under the trademark Brij 35 by Atlas Chemical Industries. The surfactant is purchased as a 30 weight percent solution and the proper dilution made. Solutions A and B are mixed in a 1:1 ratio by volume as the working reagent.

Manual Method

In practice, 2 milliliters of Solution B are pipetted into a 13×100 mm test tube, then 70 μl sample is pipetted into the tube and the contents mixed. A white cloud may appear in serum samples, but will disappear after mixing. Thereafter, 2 milliliters of Solution A are added and the test tube swirled to insure mixing.

A reagent blank solution is also prepared by adding to a 13×100 mm test tube 2 milliliters of Solution B, 70 μl of deionized water, and 2 milliliters of reagent A, followed by mixing.

For the serum sample, a serum blank solution is also prepared by pipetting 4 milliliters of deionized water into a 13×100 mm test tube and adding 70 μl of serum sample, followed by mixing.

The test procedure using the manual method is to place all solutions into a 30° C. water bath or heating block and allow them to incubate for 5 minutes. Thereafter the solutions are introduced into the spectrophotometer and readings taken when the absorbance is stable, (approximately 15 seconds).

Bichromatic Method

Any instrument that has bichromatic measurement capability such as CentrifiChem analyzer can be used with this method. In accordance with the procedure for operating the analyzer samples and reagents were pipetted into the transfer disc with a sample dilution factor of 1:40. The analyzer parameters can be dialed in manually or the computer can be programmed to do the automated experimental steps. The disc is placed inside the analyzer, parameters are loaded and spinning started. After the printout, the analyzer is then reset with wavelength changed to produce the final results.

EXAMPLES 2-9

Using the reagents prepared in accordance with Example 1, various human blood serum samples were analyzed for chloride on the CentrifiChem analyzer. The type of serum sample and the results obtained are set forth in Table I below:

TABLE I

| EXAMPLE | TYPE OF SAMPLE | $[Cl^-]$ by CORNING 920M (meq/L) | $[Cl^-]$ FOUND (meq/L) | METHOD USED |
|---|---|---|---|---|
| 2 | Normal Serum | 102 | 101 | Bichromatic |
| 3 | Iceteric Serum | 97 | 96 | Bichromatic |
| 4 | Hemolyzed Serum | 109 | 108 | Bichromatic |
| 5 | Turbid Serum | 103 | 104 | Bichromatic |
| 6 | Control Serum (500 mg/dl hemoglobin spike) | 107 | 106 | Bichromatic |
| 7 | Control Serum (43.5 mg/dl bilirubin spike) | 104 | 104 | Bichromatic |
| 8 | Deionized Water (40 meq/L $Br^-$ spike) | 32 | 1 | Bichromatic |
| 9 | Control Serum (very turbid) | 106 | 105 | Bichromatic |

EXAMPLE 10

In this example, a comparison was made of the several parameters of the invention using the bichromatic procedure and those of the manual method. Also the parameters of the hold-blank are set forth. The figures are set forth in Table II below:

TABLE II

| PARAMETERS | METHOD | | BLANK |
|---|---|---|---|
| | Bichromatic | Manual | |
| 1. Linearity | 0-120 meq/L | 0-120 meq/L | 0-180 meq/L |
| 2. Precision | | | |
| Within-day | 1.54% | 1.7% | 1.3% |
| Day-to-day | 0.8% | 1.4% | 1.8% |
| 3. Accuracy (% Recovery) | | | 95-103% |
| 4. Stability | | | 1 year at 25° C. |
| 5. Correlation with Coulmetric Method | 0.9743 | 0.968 | 0.9256 |
| 6. Interferences | | | |
| $Br^-$ | none up to 40 meq/L | | none up to 100 meq/L |
| $F^-$ | none up to 40 meq/L | | none up to 40 meq/L |
| Bilirubin | none | none up to 5 mg/dl | none up to 5 mg/dl |
| Hemoglobin | none up to 300 mg/dl | none up to 300 mg/dl | none up to 500 mg/dl |
| Turbidity | none up to grossly turbid | none up to grossly turbid | none up to grossly turbid |

Although the invention has been illustrated by the preceding examples, it is not to be construed as being limited to the materials employed therein, but rather the invention encompasses the generic area as hereinbefore disclosed. Various modifications and embodiments thereof can be made without departing from the spirit and scope thereof.

What is claimed is:

1. A process for the direct quantitative determination of chloride in blood serum which comprises the steps of:
   (a) contacting a sample of said serum with a reagent to form a solution, said reagent containing:
      (i) from about 0.01 N to about 2.0 N perchloric acid in deionized water,
      (ii) from about 0.01 N to about 1.0 N ferric perchlorate in deionized water, and
      (iii) from about 0.1 to about 20 percent by weight of an aqueous solution of a non-ionic surfactant, capable of minimizing protein precipitation while not interfering with absorbance measurement of the chloride complex;
   (b) measuring the absorbance of said solution after an incubation period,
   (c) comparing the absorbance of said solution with absorbance obtained on solutions containing known amounts of chloride, and
   (d) determining the amount of chloride in said serum.

2. The process of claim 1 wherein the absorbance of said solution is measured at 340 nm.

3. The process of claim 1 wherein interference due to the presence of bilirubin in serum blanks is eliminated by a bichromatic procedure which involves measurement at 420 nm of the bilirubin adsorption peak during its shift from 460 to 370 nm and subtracting acid measurement from the final 340 nm adsorption measurement taken on said blood serum sample.

4. The process of claim 1 wherein said non-ionic surfactant is a polyoxyethylene lauryl ether.

5. The process of claim 3 wherein said blood serum is employed in an amount of 70 microliters.

6. The process of claim 5 wherein an equal mixture by volume of deionized solutions containing 0.0756 N ferric perchlorate and 0.492 N perchloric acid are employed in a total amount of 2 milliliters.

7. The process of claim 6 wherein an aqueous solution containing 19.3 percent by weight of polyoxyethylene lauryl ether is employed in an amount of 2 milliliters.

8. A reagent useful for the direct quantitative determination of chloride in blood serum, said reagent comprised of:
 (i) from about 0.01 N to about 2.0 N perchloric acid in deionized water,
 (ii) from about 0.01 N to about 1.0 N ferric perchlorate in deionized water, and
 (iii) from about 0.1 to about 20 percent by weight of an aqueous solution of a non-ionic surfactant, capable of minimizing protein precipitation from said blood serum while not interfering with absorbance measurement of chloride.

* * * * *